US005470339A

United States Patent [19]
Lerrick

[11] Patent Number: 5,470,339
[45] Date of Patent: Nov. 28, 1995

[54] SURGICAL SCALPEL SAFETY BLADE

[76] Inventor: Andrew J. Lerrick, 232 N. Kings Hwy., #813, St. Louis, Mo. 63108

[21] Appl. No.: 309,798

[22] Filed: Sep. 21, 1994

Related U.S. Application Data

[63] Continuation of Ser. No. 55,209, Apr. 29, 1993, abandoned.

[51] Int. Cl.⁶ ..................................................... A61B 17/32
[52] U.S. Cl. ............................................... 606/167; 30/357
[58] Field of Search ...................................... 606/166, 167; 30/351, 357, 152, 294

[56] References Cited

U.S. PATENT DOCUMENTS

| D. 34,401 | 4/1901 | Herr . |
| 182,415 | 9/1876 | Coates . |
| 933,626 | 9/1909 | Coomber . |
| 3,363,315 | 1/1968 | Anderson . |
| 3,798,688 | 3/1974 | Wasson ..................................... 30/357 |
| 4,198,751 | 4/1980 | Egbert . |
| 4,290,201 | 9/1981 | Goodwin . |
| 4,763,416 | 8/1988 | Copeland . |
| 4,937,491 | 7/1990 | Crist . |
| 5,116,351 | 5/1992 | Frassetti . |

FOREIGN PATENT DOCUMENTS 1388005  4/1988  U.S.S.R. .

Primary Examiner—Stephen C. Pellegrino
Assistant Examiner—William Lewis
Attorney, Agent, or Firm—Jordan B. Bierman; Bierman and Muserlian

[57] ABSTRACT

A surgical scalpel blade made safer by providing, on the front portion thereof, a blunted surface or tip which renders the point of the blade incapable of cutting, without impeding the ability of the blade to be drawn across the surface to be incised.

8 Claims, 3 Drawing Sheets

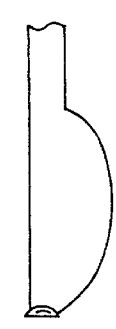
FIG.1E
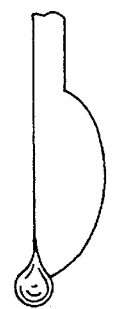
FIG.1D
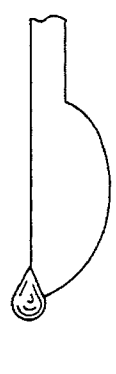
FIG.1C
FIG.1B
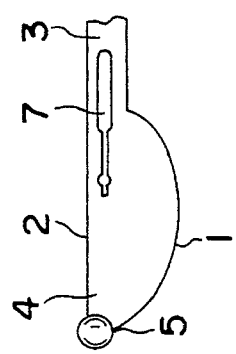
FIG.1A
FIG.1I
FIG.1H
FIG.1G
FIG.1F

SURGICAL SCALPEL SAFETY BLADE

This application is a continuation of application Ser. No. 08/055,209, filed Apr. 29, 1993, now abandoned.

The present invention is directed to a new surgical scalpel blade and, more specifically, to such a blade designed to protect medical personnel from injuries caused by the inadvertent penetration of the skin by the scalpel blade tip and cutting surface.

BACKGROUND OF THE INVENTION

A typical surgical scalpel blade is designed to be detachably attached to a surgical scalpel handle and comprises a cutting edge which culminates in a point. This point is extremely dangerous due to the sharpness thereof and oftentimes, during, for example, a transfer between the surgeon and the nurse, the tip is inadvertently caused to penetrate the flesh of either. Similarly, hasty reactions by the surgeon and the assistants after inadvertent vessel wall injury and subsequent bleeding can cause scalpel injury. In this instance, quick reaction time by the surgical team to control hemorrhaging is associated with scalpel lacerations. It is assumed by the lay person that such accidents are unavoidable as the sharp tip of the scalpel blade is essential to the cutting for which the scalpel is designed. This assumption, however, is erroneous.

Scalpel blades are designed to cut due to a backward drawing motion of the sharp edge of the scalpel against the surface to be cut. The curved belly of the scalpel blade makes its cutting motion unique. The preferred method of incising the skin is with the belly of the blade, although, some surgeons prefer to use, exclusively, the point of the blade. Thereafter, the belly of the blade does nearly all the sharp dissection of the underlying soft-tissue. Scalpels, which are controlled by finger motion, are not used in conjunction with stabbing or hacking motions as is the case with hand-held knives. Thus, the tip of the scalpel can be modified to prevent the point from inadvertently stabbing hospital personnel without compromising its cutting ability. At the same time, however, the modification must be one that does not prevent the drawing of the blade necessary to make an incision by creating substantial drag or resistance. Although innovations have been made in surgical scalpels to decrease handling of the sharp blades during the changing thereof, Applicant surprisingly found that no attempts to increase the safety of the scalpel during its use were previously made by improving the design of surgical scalpel blade tips, by modifying the shape of the cutting surface belly, by shielding the tip, or by changing the angle thereof. Nor had anyone previously created a top finger or clamp gripping surface on the blade.

BRIEF DESCRIPTION OF THE INVENTION

In view of the foregoing, it is an object of the present invention to provide a scalpel blade which will protect against inadvertent puncture wounds and, at the same time, will not impair the ability of the blade to be drawn across the surface which is to be cut.

It is a further object of the invention to provide a scalpel blade which will deflect previously cut surfaces away from the belly of the blade and which can be further used to make cuts of a controlled depth by effectively shielding deeper tissues from the cutting edge.

It is a further object of the invention to supply a scalpel blade that can act as a retractor while effectively protecting adjacent tissue.

It is yet a further object of the invention to provide a scalpel blade that has a top surface that allows for finger or clamp gripping to give a secure hold during blade changes.

Other objects and features of the present invention will become apparent from the following detailed description considered in conjunction with the accompanying drawings.

BRIEF DESCRIPTION OF THE DRAWINGS

FIGS. 1a to 1h illustrate side views of various embodiments of the invention incorporating different shaped tip shields and various blade designs;

FIG. 1i shows an oblique side view of an inventive blade with a modified second edge surface.

DETAILED DESCRIPTION OF THE INVENTION

Figure 2:
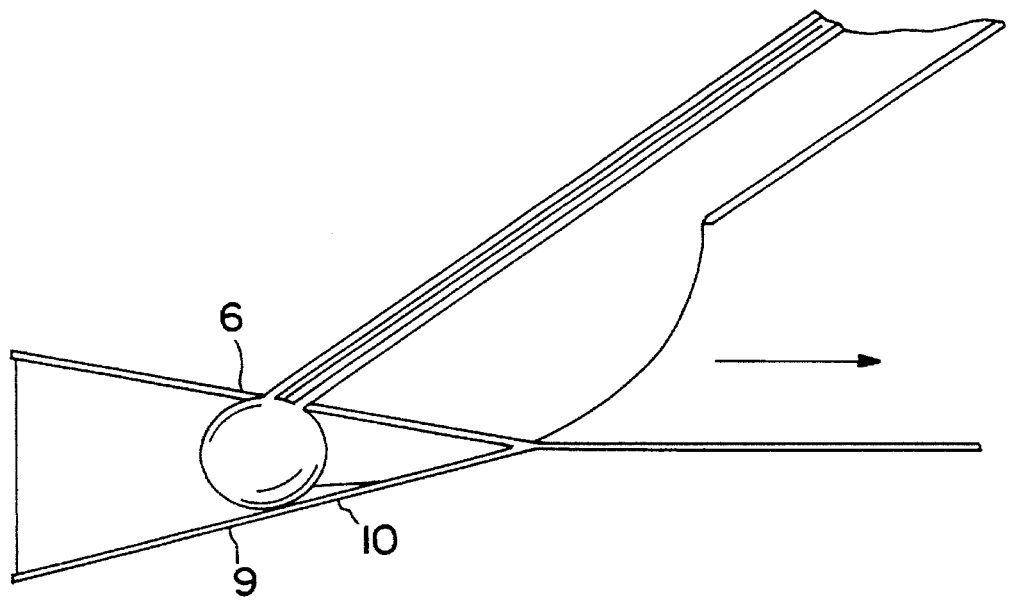
FIG. 2 shows the manner in which the inventive scalpel is used in conjunction with deflection cutting.

An inventive surgical scalpel blade is illustrated in FIG. 1a. The inventive blade is defined by a first edge surface 1 adapted to cut when drawn across the tissue in which an incision is to be made. Opposite first edge surface 1 is second edge surface 2; the proximal ends of the first and second surfaces end at a proximal end portion 3 adjacent to the scalpel handle.

Distal ends of first edge surface 1 and second edge surface 2 meet at distal end portion 4 of the blade, which is remote from end portion 3. Distal end portion 4 has edge surface 5 modified to be incapable of cutting. At the same time, this modification of edge surface 5 of distal end portion 4 cannot impede the drawing of the blade across the surface being cut.

To render edge surface 5 of distal end portion 4 incapable of cutting, distal end portion 4 can be blunted; however, it is preferable that, at the same time edge surface 5 is formed with an increased thickness. Preferably, the thickness of edge surface 5 is increased by positioning smooth non-penetrating contoured tip 6 on distal end portion 4 of the blade. By forming tip 6 with a smooth, rounded contour, the tip can be made to deflect the previously cut surface away from the belly of the blade. Tip 6 can be spherical as shown in FIG. 1a, and can be varied in size as illustrated by FIG. 1b. The shape of tip 6 is not limited to that of the sphere, but can also be formed in the shape of a teardrop (FIG. 1c), a modified teardrop (cone-shaped as shown in FIG. 1d), or a halved sphere (FIG. 1e). The only limitation on the shape of tip 6 is that it does not impede the drawing of the blade across the surface being cut. The inventive blade can have the traditional design for handle attachment or can have attachment portion 7 adapted to permit attachment of the scalpel blade to a scalpel handle (not shown). It is also possible to form the blade integrally with a handle.

Second edge surface 2 can curve downward at distal end portion 4 so that tip 6 is provided below the plane of second edge surface 2 (see FIG. 1f). By so forming the blade, the probability of a head-on approach is reduced further preventing operating room personnel from receiving inadvertent cuts. In addition, second edge surface 2 can be provided with widened portion 12 to form a surface on which the user's finger can at least partially rest, to better guide the blade (see FIG. 1g). The belly of the blade can have either the traditional shape, or a diminished curvature (see FIG.

1h), which will expose less cutting surface and decrease the chance of a penetrating injury. A smooth wave formed on second edge surface 2 can also be provided to form a secure finger or clamp hold useful during blade changes. Second edge surface 2 can, thus, be straight, or alternatively, wavy (see FIG. 1i).

Figure 3:
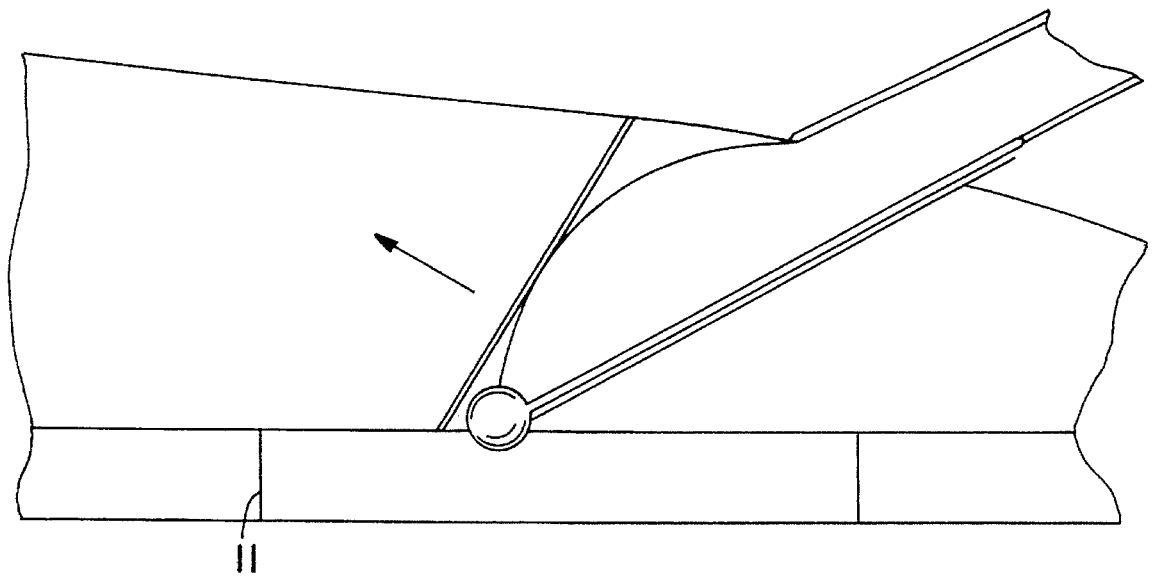
FIG. 3 demonstrates the use of the inventive scalpel blade in a protective cutting procedure.
Figure 4:
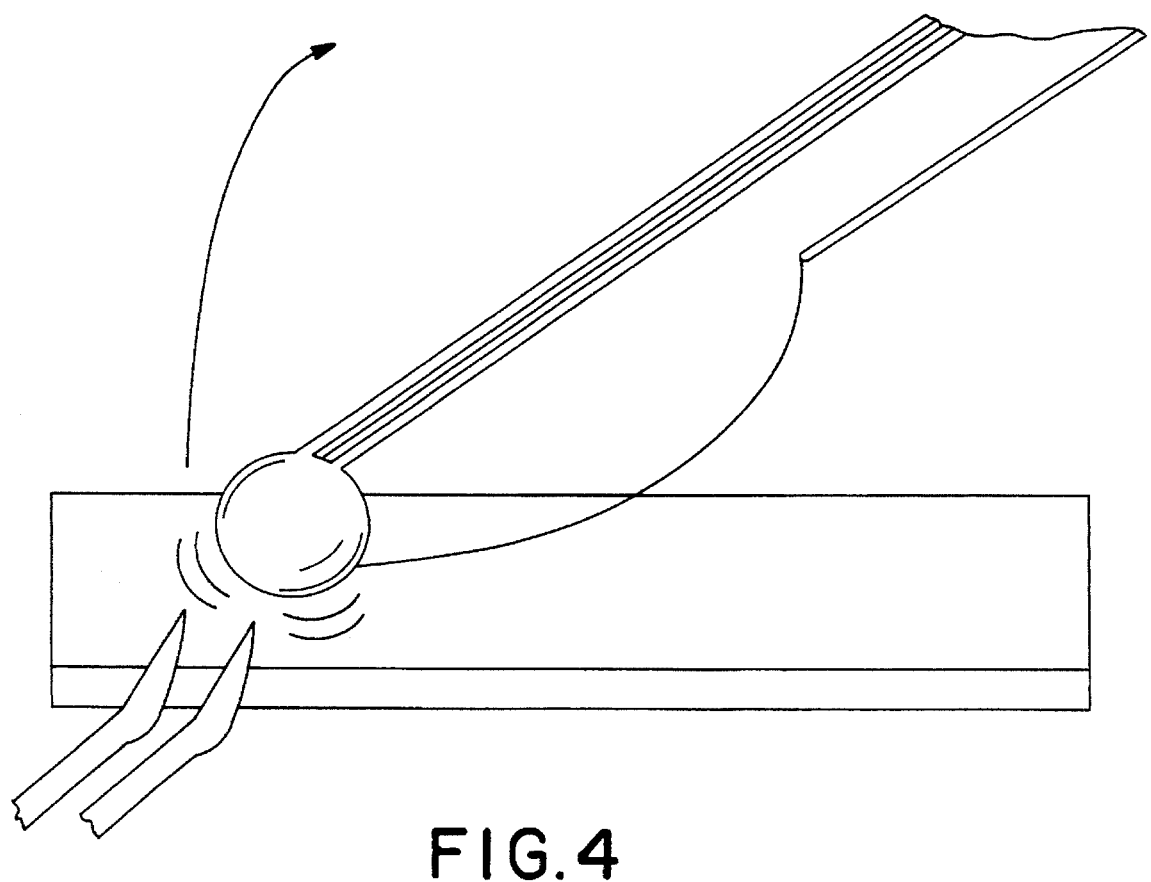
FIG. 4 shows the use of the inventive blade in retraction.

FIG. 2 illustrates the use of the inventive blade in normal deflection cutting and, as is clear therefrom, tip 6 can effectively deflect previously cut tissue 9 away from the belly of blade 10 during cutting so the depth of the cut can be more accurately gauged. In protective cutting, as shown in FIG. 3, the scalpel can be used upside down and effectively shields deeper tissues 11, such as blood vessels, nerves, and tendons from the cutting surface. With a conventional blade such cuts are extremely hazardous as the deeper tissue is easily nicked by the exposed point of the conventional scalpel. FIG. 4 illustrates the use of the inventive blade as a retractor, again effectively protecting adjacent tissue during retraction.

Thus, because of tip 6, the inventive blade has a number of advantages over those heretofore used. It can prevent inadvertent puncture injuries to operating room personnel and, at the same time, allow the user to more accurately make incisions, while shielding surrounding tissue from the cutting edge of the blade. The ability of the blade to be drawn along the surface to be cut is not impaired. The inventive blade can be used in either deflection or protective cutting procedures, and can also be employed as a retractor.

While only the fundamental novel features of the invention as applied to a preferred embodiment thereof have been shown and described, it is understood that various omissions, substitutions, and changes in the form and details of the device illustrated and in its operation may be made by those skilled in the art without departing from the spirit of the invention. It is therefore the intention of Applicant that the invention be limited only as indicated by the scope of the claims appended hereto.

I claim:

1. A surgical scalpel blade defined by a sharpened first edge adapted to cut by drawing along a surface to be incised, a second edge opposite said first edge, a proximal end portion at a proximal end of said first edge and a proximal end of said second edge being adapted to accept a scalpel handle, and a distal end portion at which a distal end of said first edge and a distal end of said second edge meet at a juncture, a tip portion having a cross section greater than that of said blade being provided at said juncture, the greater cross section of said tip portion rendering said distal end of said first end incapable of cutting, said first edge of said blade having a belly portion extending further from said second edge than said tip portion, whereby the drawing of said blade is substantially unimpaired by said tip portion, said second edge being straight, said first edge curving from said belly portion toward said first edge at said distal end portion.

2. The blade of claim 1 wherein said tip portion is a sphere.

3. The blade of claim 1 wherein said tip portion is a cone.

4. The blade of claim 1 wherein said tip portion is a teardrop.

5. The blade of claim 1 wherein said tip portion is a half sphere with an exposed surface facing said proximal end portion.

6. The blade of claim 1 wherein said second edge curves toward said first edge, and said first edge curves toward said second edge at said distal end portion.

7. The blade of claim 1 wherein said second edge surface has an increased thickness.

8. The blade of claim 1 wherein said second edge surface is wavy.

\* \* \* \* \*